United States Patent [19]

Adelman

[11] Patent Number: 5,656,429
[45] Date of Patent: Aug. 12, 1997

[54] POLYNUCLEOTIDE AND PROTEIN ANALYSIS METHOD USING MAGNETIZABLE MOIETIES

[76] Inventor: Lonnie W. Adelman, 4565 - 62nd St., San Diego, Calif. 92115

[21] Appl. No.: 316,772

[22] Filed: Oct. 3, 1994

[51] Int. Cl.$^6$ .............................. C12Q 1/68; C12P 19/34; G01N 11/00; G01R 33/00
[52] U.S. Cl. .............. 435/6; 435/91.2; 324/260; 73/54.18
[58] Field of Search ............... 435/6, 91.2; 324/260; 73/54.18

[56] References Cited

U.S. PATENT DOCUMENTS 4,219,335  8/1980  Ebersole ................................. 23/230

FOREIGN PATENT DOCUMENTS

WO91/09141 of 1991 WIPO.
WO93/10162 of 1993 WIPO.

OTHER PUBLICATIONS

Southern, (1975), "Detection of specific sequences among DNA fragments separated by gel electrophoresis", J. Mol. Biol. 98:503–517.
Darnell et al, (1986), "Molecular Cell Biology", pp. 233–236.
Dynal catalog, (1995), pp.2–6.
Stacy et al, (1991), "Fingerprinting of diverse species with DNA probes generated from immobilized single-stranded DNA templates", Nucleic Acids Res. 19(14):4004.
Dudin et al, (1988), "Sorting of chromosomes by magnetic separation", Hum. Genet. 80:111–116.
Olsvik et al, (1994), "Magnetic separation techniques in diagnostic microbiology", Clin. Microbiol. Res. 7(1):43–54.
Brinchman et al, (1988), "Direct immunomagnetic quantification of lymphocyte subsets in blood", Clin. Exp. Immunol. 71:182–186.
Journal of Food Protection, vol. 55, Mar. 1992, "Isolation of Escherichia coli 0157:H7 Using Specific Antibody Coated Magnetic Beads" by Anita J.G. Okrend, Bonnie E. Rose, and Charles P. Lattuada.

Electrophoresis 1992, pp. 587–595, "Laterally aggregated polyacrylamide gels for electrophoresis" by P.G. Righetti et al.

Publication "Advance for Medical Laboratory Professionals" dated Aug., 1994, Article by Heide K. Lang Lab's Role Crucial to Outcome —Murder Trial of the Century.

Microplate Equipment/Electrophoresis/Application Note "An Electrochemiluminescence-based detection system for quantitative PCR" by M.S. Anderson, J.L. Di Cesare, and E.D. Katz.

Letters in Applied Microbiology 1993, 16, pp. 122–125 "Immunomagnetic separation as an alternative to enrichment broths for Salmonella detection" by Lucielle P. Mansfield and S.J. Forsythe.

*Primary Examiner*—George G. Elliott
*Assistant Examiner*—Jeffrey Fredman
*Attorney, Agent, or Firm*—McAulay Fisher Nissen Goldberg & Kiel, LLP

[57] ABSTRACT

A method for sequencing nucleotides by attaching magnetizable moieties to the components of a mixture of such polynucleotide proteins and fragments, subjecting the mixture to a separation procedure to distribute the compounds on a substrate in a pattern according to molecular size and quantity, imparting magnetic properties to the attached magnetizable moieties, and then subjecting the substrate to magnetic reading to determine the molecular size and quantity of the compounds. Also disclosed is a method for monitoring a molecule amplification process wherein primers are used to produce copies of a molecule, which primers become part of the copy of the molecule by attaching a magnetized moiety to each primer such that the copy has magnetizable moieties at each end. The magnetizable moieties may then be magnetized. By subjecting the mixture to a magnetic field, the primers in the mixture can be separated from the copies produced and then the copies produced can be analyzed by a magnetic field sensor to determine the amount of copies produced.

7 Claims, No Drawings

POLYNUCLEOTIDE AND PROTEIN ANALYSIS METHOD USING MAGNETIZABLE MOIETIES

BACKGROUND OF THE INVENTION

The invention relates to the field of amplification and sequencing of polynucleotides and/or proteins as well as fragments of such compounds. More particularly, it relates to methods for analyzing their structure and molecular weights as well as monitoring the progress of processes wherein such compounds are made.

There is an increasing demand for reliable and inexpensive methods for the sequencing of polynucleotides, such as, DNA, RNA and the like. Generally, a radioactive or fluorescent probe, which selectively hybridizes to a specific target nucleic acid, is added to the support. A typical common type of probe is a single-stranded (ss) DNA which is complementary to a sequence in the target DNA or RNA.

The hybrid molecule thus formed with the label probe thereon may then be detected by various techniques depending on the nature of the label used. An example of such hybridization is shown in U.S. Pat. No. 4,358,535.

Typical labelling probes include the incorporation of a radioactive atom, such as, $^{32}P$, $^{14}C$, or $^{3}H$. This can be achieved by nick translation, such as that shown in Rigbny et al (J. Mol. Biol., 113:237, 1977), wherein a labelled nucleotide is incorporated into a gap created in the DNA of the probe. Other labels can be introduced by nick translation, for example, by incorporating biotinylated nucleosides which can then be coupled to an avidin bound label, such as, an enzyme. The DNA can also be labelled with antigenic groups reacting with antibodies.

For the assay or quantification of nucleic acids, such as, DNA or mRNA, either the total nucleic acid material present in the sample or that transcribed from a specific gene can be conventionally determined by this so-called dot-blot analysis technique.

One of the problems with such sequencing techniques requires the handling of radioactive isotopes and presents an environmentally undesirable situation in the laboratory. The use of fluorescent labels or enzyme labels results in relatively complicated techniques for the ultimate reading of the label. Generally, expensive equipment and relatively skilled technicians are needed to effect the analysis of gels and/or substrates onto which the labelled molecules or segments have been fixed.

In addition, numerous attempts have been made to automize the electrophoresis step, detection and data handling. However, difficulties have arisen with respect to such methods primarily because of the method of labelling.

The present invention also relates to methods for the amplification, i.e., duplication of polynucleotides, such as, DNA. Numerous methods for duplication have arisen. These include the so-called polymerase chain reaction (PCR) which is based on the phenomenon known as primer extension by DNA polymerases. In this method, an oligonucleotide having a size of 15 to 20 base-pairs is used as a primer which is complementary to the 5' end of each strand of a sequence tagged site. The primer is mixed in excess with a DNA sample from a target sequence (STS) to be amplified. The 4-deoxyribonucleoside triphosphates are also provided. The reaction mixture is then taken through a sequence of multiple synthetic cycles which consist of a first denaturization to take apart the two strands of DNA and create a set of single stranded templates, annealing by cooling to encourage the primers to anneal to their complementary sequences on a single stranded templates, and then heating to activate the polymerase which results in extension of a new DNA strand.

The reaction mixture is normally taken through a multiple of such synthesis cycles depending on how much amplification is desired. It is desirable to be able to determine at some point during the process the status of the synthesis, i.e., how much new DNA has been produced. To date, the methods provided for such determination have generally not proven satisfactory.

SUMMARY OF THE INVENTION

I have discovered a method for sequencing nucleotides which substantially alleviates the problems previously encountered in analyzing mixtures of nucleotides. In particular, I have discovered that by attaching magnetizable moieties to the components of a mixture of such polynucleotides, proteins, and fragments thereof, normally obtained from enzymatic digestion, one can easily determine both the quantity as well as the magnetic size (generally in terms of magnetic weight or dalton size, or (base-pairs) of the polynucleotides, proteins and fragments by reading the magnetic field created by the attached magnetizable moieties.

This is accomplished by subjecting the mixture of polynucleotides, proteins and fragments to a separation procedure to distribute the compounds onto a substrate in a pattern or groups, according to their molecular size and quantity. This substrate is then analyzed to determine the molecular size and quantity on the separated groups. Magnetizable moieties are attached to each of the components of the mixture. This attachment may occur prior to subjecting the mixture to the separation procedure or after the separation. The magnetizable moieties are then magnetized by exposing them to a magnetic field. This magnetization step may also take place either before or after the separation procedure is carded out. The thus separated compounds having the attached magnetized or magnetizable moieties thereon are distributed onto a substrate, such that the groups distributed are separated on the substrate according to molecular size and amount. This substrate is then subjected to magnetic reading, such as by a disk reader or other type of means for reading a magnetic tape or disk. Based on the magnetic reading, both the size and amount of each of the groups thus distributed may be ascertained by appropriate calibration methods.

In yet another embodiment of the invention, I have discovered a method for monitoring the procedure for amplification of molecules, such as, polynucleotides. In such amplification methods, first and second primer segments are mixed with a starting molecule. These primer segments, as is known, result in the production of a multiplicity of copies of the starting molecule. Each copy thus produced has a first and second primer attached thereto.

In the inventive method, a magnetizable moiety is attached to each of the first and second primer segments prior to mixing the primer segments with the starting molecule. The magnetizable primer segments are then subjected to magnetization conditions, i.e., by subjecting them to a magnetic field prior to carrying out the amplification reaction. The reaction is then carried out. At an interim point beginning and end of the reaction cycle, the progress of the reaction is monitored by measuring the number of copies of the molecule produced. This is accomplished by subjecting the reaction mixture to a magnetic field to separate the duplicate copies produced from the magnetized primers in the mixture. The separated copies are then measured to determine the strength of the magnetic field due to the separated copies. Suitable calibration means can then be used to interpret the strength of the magnetic field of the separated copies in terms of the amount of separated copies thus produced.

DETAILED DESCRIPTION OF THE INVENTION

The first embodiment of the invention wherein a mixture of varying mounts of nucleotides, proteins and the like, are analyzed will be described in connection with the sequencing of DNA. It is known to subject DNA obtained from cells and the like to digestion with various enzymes which cleave the DNA at different sites. Thereafter, the library obtained from the enzymatically digested DNA is subjected to separation analysis usually by electrophoresis on an agarose or polyacrylamide gel. Such electrophoresis methods are also well known in this art. During electrophoresis, the various segments travel along the gel, usually in a downward direction, depending on the magnetic field applied, and travel relative to their molecular size. Normally, the larger molecular size molecules travel less distance than the smaller molecules. This also can depend on the pore size of the gel and variation of these parameters is well known to the artisan in this field.

At the end of the procedure, the various fragments of the digested DNA are present on the gel in a pattern determined by their distance of travel during the electrophoresis process. The distance of travel is directly related to the molecular size of the fragment. In addition, the size of each group of segments or fragments on the gel is indicative of the amount of the specific component in the original mixture.

I have discovered that the fragments of the digested DNA can be attached to magnetizable moieties, either prior to or subsequent to the electrophoresis process. In the instance where the fragments are attached prior to electrophoresis, the attachment of magnetizable moieties is carried by known procedures, such as, as described in PCT applications WO 92/17609 published Oct. 15, 1992; WO 93/08305 published Apr. 29, 1993; WO 90/06042 published Jun. 14, 1990; and WO 93/20232 published Oct. 14, 1993. See also, PCT/EP90/00454, PCT/GB89/00304, and PCT/EP91/01398. In addition, techniques for attachment of magnetizable moieties are also disclosed in the Technical Handbook Molecular Biology, 1st Ed., Dynabeads Biomagnetic Separation System, published by Dynal International. This brochure describes various methods for the biotinylation of DNA as well as the sequencing of biotinylated DNA. Detailed procedures are presented therein.

The DNA with the magnetic moieties attached thereto as carried out, for example, as described in the above-noted disclosures, is then subjected to magnetization by placement in a magnetic field. The magnetization can be carried out in a conventional manner which is also disclosed in the above Technical Handbook Molecular Biology.

As noted, the magnetization step can be carried out either prior to the electrophoresis analysis by subjecting the mixture of DNA having the magnetic moieties attached thereto to a magnetic field, or after the electrophoresis procedure by subjecting the gel on which the groups of DNA segments having the magnetizable moieties attached thereto have been distributed, by for example, using an electromagnet.

Alternatively, the electrophoresis procedure can by carried out on the digested DNA mixture in the conventional manner. Thereafter, the distributed DNA segments on the gel may be treated so as to attach the magnetizable moieties thereto. In addition, it is possible to carry out the digestion and electrophoresis in the conventional manner and then transfer the groups of electrophoresed DNA segments onto a substrate using conventional Southern blot hybridization techniques. Such techniques are well known in the art and result in the electrophoresed groups of DNA being transferred to a second substrate, usually a sheet.

This sheet, in turn, may be contacted with a sheet containing magnetizable and/or magnetized probes which are selected for specific DNA sequences. The probes thus hybridize to the DNA sequences for which they are selective. This results in a substrate having magnetized or magnetizable portions of groups of DNA segments thereon.

Whichever of the foregoing procedures is used, ultimately a sheet, either of a gel or a transfer sheet as obtained by a blotting method, is produced which contains the distributed DNA segments having magnetized moieties attached thereto. The groups of DNA segments are distributed on the sheet according to their molecular sizes and the sizes of the groups are indicative of the amount of such segments in the original digested mixture.

This substrate may then be subjected to conventional magnetic reading analysis, for example, with devices used to read magnetic cards, magnetic floppy disks, magnetic tapes, and the like. By appropriate calibration techniques, the reading of the magnetic field created by each of the respective groups distributed on the substrate will be indicative of the specific DNA segment as the molecular size of that DNA segment.

In particular, it is clear that such substrates having the magnetized groups thereon, may be formed into the shape of a so-called "floppy disk" and read by computer. Appropriate computer programs can easily be formulated to immediately provide a readout as to the molecular size and amount of the specific segments being read.

I have specifically discovered that the magnetization of such magnetizable moieties does not disappear after magnetization. That is to say, a residual amount of magnetization remains sufficient to allow reading of the magnetic field of the specific moieties as distributed on the substrate.

By using such magnetic labels for reading, i.e., sequencing DNA and the like molecules, it becomes possible to completely avoid the difficulties which have arisen using the fluorescent, enzyme and radioactive labels of the prior art. In addition, extremely accurate readings of both the molecular size and amount of the segments deposited on the substrate are possible.

In yet another embodiment of the invention, I have found that by using magnetic moieties as primers in a DNA amplification process, one can easily monitor the progress of the amplification process. A variety of methods for DNA amplification which use primers are known in the art. See, for example, the Journal of NIH Research, January 1953, Vol. 5. In an article entitled "PCR's Competitors Are Alive and Well and Moving Rapidly Towards Commercialization", the alternative methods to the so-called polymerase chain reaction are described. These various processes use primer molecules for the purpose of growing entire sequences of DNA. In each of these type processes, it is desirable to have the ability to monitor the progress of the reaction and determine the amount of DNA that has been produced at any given time.

I have discovered a method for facilitating the monitoring of such amplification reactions. Two primers generally act in such amplification procedures to form a single molecule of DNA. The resulting molecule thus produced has a primer at each terminus. When the primers have magnetic moieties attached thereto, each such copy of DNA thus produced will have a magnetizable moiety at each of its terminal points. The magnetic moieties attached to the primers can be subjected to magnetization conditions prior to the amplification reaction to render the moieties magnetic. Alternatively, the mixture during the amplification reaction can be subjected to magnetization conditions, although the former procedure wherein the primers are subjected to magnetization prior to the reaction is preferred.

Normally, the amplification procedures are carried out in receptacles or containers, such as small test tubes and the like. The test tubes containing the reaction mixtures are placed in an appropriate temperature cycling device which subjects these mixtures to the multiple temperature cycles required for the amplification procedure.

At an interim time during the amplification procedure, the contents of the receptacle, i.e., the reaction mixture can be subjected to a magnetic field, i.e., by use of an electromagnet to separate the magnetized primer elements from the formed DNA sequences having the magnetizable moieties at each terminus. Normally, in a tube which is held in a vertical position, if the electromagnetic field is positioned close to the bottom of the tube, the primers, being lighter than the completed strands of DNA, travel faster than the completed strands within the reaction mixture and collect at the bottom of the tube. This leaves the completed DNA strands with the magnetized moieties at the respective terminus ends in a position toward the tube midpoint.

Using appropriate known devices, the size of the magnetic field created by the produced sequences, can be measured. This can be easily correlated to the total amount of DNA which has been produced at that point. Typical of devices which can be used to measure the magnetic field created by the completed DNA sequences are so-called "Hall" sensors. See Sensors, March 1986, published by North American Technology. Such so-called Hall sensors, when placed in a magnetic field oriented at right angles to the Hall current, measure a voltage output which is in direct proportion to the strength of the magnetic field. The measurement of the magnetic field thus produced by the completed DNA copies can easily be correlated by appropriate predetermined correlation charts to the amount of DNA produced from the amplification procedure. Of course, other types of devices which can measure Hall effect sensors can be used.

What is claimed is:

1. A method for analyzing a mixture of varying amounts of compounds having different molecular sizes, said compounds being selected from the group consisting of polynucleotides, proteins, and fragments thereof, wherein the mixture is subjected to a separation procedure to distribute the compounds therein on a substrate in a pattern of groups according to molecular size and quantity, and then analyzing the substrate to determine the molecular size and amount of compounds in the thus separated groups, the improvement which comprises:

attaching magnetizable moieties to each of the components of the mixture, imparting magnetic properties to the attached magnetizable moieties to convert them to magnetized moieties, and then subjecting the substrate with the distributed groups of compounds with the attached magnetized moieties to magnetic reading to determine the molecular size and amount of the compounds in each of the groups.

2. The method of claim 1 wherein the magnetizable moieties are attached to the compounds prior to subjecting the mixture to the separation procedure.

3. The method of claim 1 wherein the magnetizable moieties are attached to the compounds after the mixture has been subjected to the separation procedure.

4. The method of claim 1 wherein the separation procedure is electrophoresis.

5. The method of claim 1 wherein the compounds are polynucleotides selected from the group consisting of DNA and RNA.

6. The method of claim 1 wherein the compounds are proteins.

7. The method of claim 1 wherein the compounds are polynucleotides obtained from the digestion of cellular DNA, the separation procedure is electrophoresis and the groups of compounds are distributed in a pattern onto a gel sheet, and the gel sheet is subjected to Southern hybridization to transfer DNA on the gel sheet to a second sheet, treating the second sheet with the DNA thereon to attach the magnetizable moieties to the DNA, and then subjecting the second sheet to magnetic reading.

* * * * *